(12) United States Patent
Paul et al.

(10) Patent No.: US 6,441,221 B1
(45) Date of Patent: Aug. 27, 2002

(54) METHOD FOR CONDITIONING LONG CHAIN ALKYL ACRYLATES

(75) Inventors: Jean-Michel Paul, Metz; Jean-Paul Gamet, Savy Berlette, both of (FR)

(73) Assignee: Atofina, Puteaux (FR)

( * ) Notice: Subject to any disclaimer, the term of this patent is extended or adjusted under 35 U.S.C. 154(b) by 0 days.

(21) Appl. No.: 09/581,574

(22) PCT Filed: Dec. 10, 1998

(86) PCT No.: PCT/FR98/02690

§ 371 (c)(1),
(2), (4) Date: Jul. 10, 2000

(87) PCT Pub. No.: WO99/31042

PCT Pub. Date: Jun. 24, 1999

(30) Foreign Application Priority Data

Dec. 15, 1997 (FR) .............................................. 97 15874

(51) Int. Cl.[7] .............................................. C07C 69/54
(52) U.S. Cl. ........................................ 560/205; 560/218
(58) Field of Search .................................. 560/205, 218

(56) References Cited

U.S. PATENT DOCUMENTS 4,650,596 A * 3/1987 Schlueter et al. .......... 252/51.5
5,039,432 A * 8/1991 Ritter et al. ................. 252/8.3

FOREIGN PATENT DOCUMENTS

| EP | 0 013 836 | 8/1980 |
|---|---|---|
| FR | 2 224 437 | 10/1974 |
| FR | 2 602 229 | 2/1988 |

* cited by examiner

*Primary Examiner*—Paul J. Killos
*Assistant Examiner*—Zachary C. Tucker
(74) *Attorney, Agent, or Firm*—Millen, White, Zelano & Branigan, P.C.

(57) ABSTRACT

The invention relates to a process for packaging long-chain alkyl acrylates by mixing them with a sufficient amount of solvent, e.g. xylenes, ethylbenzenes or trimethylbenzenes, thereby facilitating the handling of said acrylates by reducing the melting point of the mixture.

35 Claims, No Drawings

METHOD FOR CONDITIONING LONG CHAIN ALKYL ACRYLATES

The present invention relates to a process for packaging long-chain alkyl acrylates.

Acrylates of a long-chain alkyl, i.e. of an alkyl in which the number of carbon atoms is at least 18, are used as comonomers in formulations intended to lower the setting point of paraffinic oils. Crude oils can contain paraffins whose nature and content are directly linked to the site of extraction. At a temperature which depends on the nature of the oils, there is crystallization of these paraffins, which leads to a decrease in their fluidity with, as a consequence, an inconvenience in their transportation and storage. One advantageous solution consists in lowering the setting point of these oils by adding an additive. French patent FR-A-1 575 984 has proposed the use of macromolecular compounds of comb type constructed on the model of a hydrocarbon-based chain bearing fairly long ($C_{14}$ to $C_{30}$) side chains. Other patents, such as French patent FR-B-2 128 589 and U.S. Pat. No. 2,839,512, claim the use of copolymers of $C_{18}$–$C_{30}$, preferably $C_{18}$–$C_{22}$, acrylates and of a heterocyclic monomer of vinylpyridine type. International patent application WO 97/34940 claims the use of acrylic copolymers prepared from linear $C_{24}$ to $C_{60}$ (preferably $C_{30}$ to $C_{40}$) acrylates and from $C_{10}$ to $C_{22}$ acrylates (for example behenyl acrylate).

The problem which the invention aims to solve is as follows:

Long-chain ($>C_{18}$) alkyl acrylates, which are useful in the context which has just been indicated, are difficult to handle due to the fact that they are solids with a high melting point. Their handling requires them to be and to be maintained in liquid form (above their melting point). They should be stored in heated containers or in heatable drums or barrels.

When they are stored in heated containers, it is necessary, on account of their high melting point, to keep them at high temperature, which is restrictive and hazardous (risks of polymerization);

when they are packaged in drums, long and laborious high-temperature melting operations in heated chambers are required before use, with the ensuing risks of polymerization.

The Applicant Company has attempted to find a solution to facilitate the handling of long-chain alkyl acrylates while at the same time reducing the risks of polymerization, and it proposes, in accordance with the present invention, a packaging process leading to a product consisting of a mixture of the said acrylate and of a solvent, which mixture has a lower, and in particular markedly lower, melting point than that of the said acrylate. The handling of this mixture is thus made all the more easy and the risks of polymerization during melting of the product are substantially reduced; in this presentation form, the said acrylate can be packaged in liquid form at low temperature in heated containers without any risk of polymerization; it can also be stored in drums and melted during its subsequent use in total safety.

Moreover, the said solvent can already, in a very advantageous manner, be introduced into the reactor for synthesizing the said acrylate, another advantage of the invention then consisting of a greater ease of emptying the crude reaction mixture out of the reactor. Thus, lowering the melting point has a proportionate effect on preventing the risks of crystallization of the product when it is emptied from the reactor into the pipes for transferring it to the containers or drums.

A subject of the present invention is thus a process for packaging a long-chain alkyl acrylate of general formula:

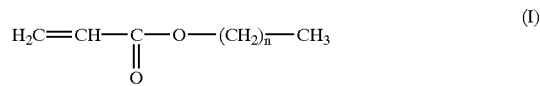

in which n is between 18 and 60, it being possible for the said acrylate also to be in the form of a mixture of acrylates (I) having chain lengths of between 18 and 60 carbon atoms, characterized in that a mixture of the said acrylate (I) and a solvent (SL) is formed whose nature and amount are chosen such that the said mixture constitutes a product whose melting point is less than that of the said acrylate (I).

In accordance with one preferred embodiment of the process according to the present invention, the solvent (SL) is introduced into the reactor for manufacturing the acrylate (I) during the loading of the reagents and/or during the reaction and/or after the end of the reaction, the said solvent (SL) being chosen such that it is inert with respect to the reaction medium into which it is introduced. The solvent (SL) can thus be chosen from aliphatic or aromatic hydrocarbons, such as petroleum hydrocarbon fractions. Specific examples of solvents (SL) which may be mentioned are xylenes, ethylbenzenes and trimethylbenzenes.

The solvent (SL) is advantageously introduced in an amount such that it represents from 10 to 70% by weight, in particular from 40 to 70% by weight, relative to the acrylate (I).

In the case of a process according to the present invention combined with the manufacture of the acrylate (I) by transesterification between a light ester, which is liquid at room temperature, of formula (II):

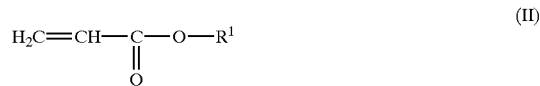

in which $R^1$ represents $C_1$–$C_4$ alkyl and a heavy alcohol, which is solid at room temperature, of formula (III):

in which n is from 18 to 60, in the presence of at least one transesterification catalyst and at least one polymerization inhibitor, while bubbling with air or depleted air, the light alcohol $R^1OH$ formed distilling off in the form of an azeotrope of light ester (II)/$R^1OH$, and the excess light ester (II) being removed by distillation at the end of the reaction, the solvent (SL) can be added to the initial load and/or after removal of the light ester (II), the said solvent (SL) having a boiling point which is greater than that of the light ester (II) when it is introduced in total or in part with the initial load.

The transesterification is moreover carried out under the standard conditions, i.e. in a molar excess of light acrylic ester (II), the ester (II)/alcohol (III) molar ratio generally being between 1.1 and 6 and more particularly between 1.1 and 3.5, a high molar ratio being favourable to the conversion of the alcohol (III) but penalizing as regards the production efficiency. The transesterification temperature is generally between 80 and 160° C.

As indicated above, the transesterification is generally carried out in the presence of a catalyst such as dibutyltin and the other products of this family including, for example, distannoxanes, titanates such as, for example, isopropyl titanate, sodium, calcium and magnesium alkoxides, zirconium and calcium acetylacetonates and other products of this family. The amount of catalyst used is between 0.001 and 0.05 mol per 100 mol of alcohol (III), and preferably between 0.001 and 0.01 mol per 100 mol of alcohol (III).

Also as indicated above, the transesterification is generally carried out in the presence of at least one polymerization inhibitor chosen from the following products that are well known to those skilled in the art: phenothiazine, hydroquinone, hydroquinone methyl ester, di-tert-butyl-catechol, in a proportion in particular of from 0.05 to 0.5% by mass, calculated on the basis of the alcohol (III).

In the case of a process according to the present invention combined with the manufacture of the acrylate (I) by esterification between acrylic acid and the heavy alcohol, which is solid at room temperature, of formula (III):

$$CH_3(CH_2)_nOH \quad (III)$$

in which n is from 18 to 60 in the presence of at least one esterification catalyst and of at least one polymerization inhibitor and in a light solvent (Sl) which is capable of forming an azeotrope with water, the reaction water distilling off in the form of an azeotrope of light solvent (Sl)/water, the solvent (SL) can be added to the initial load and/or at the end of the esterification reaction, the said solvent (SL) having a boiling point which is higher than that of the light solvent (Sl) when it is introduced in total or in part with the initial load.

The esterification is moreover carried out under the standard conditions, the alcohol (III)/acrylic acid molar ratio generally being between 1.05 and 5, and the temperature being between 80 and 160° C. The light solvent (Sl) facilitates the removal of the water by forming an azeotrope with it, shifting the esterification equilibrium in the direction of formation of the acrylate (I). It can be chosen in particular from aliphatic and aromatic solvents which form an azeotrope with water, for example hexane, cyclohexane and toluene.

As indicated above, the esterification is generally carried out in the presence of a catalyst chosen, for example, from strong inorganic acids such as $H_2SO_4$ or methanesulphonic acid, and cationic ion-exchange resins in $H^+$ form, for example the cationic resins obtained by sulphonating a copolymer of styrene and of divinylbenzene, having $H^+$ contents of between 0.05 and 0.2 equivalent/kg of reagents.

Similarly, the esterification is generally carried out in the presence of a polymerization inhibitor, such as those indicated above for the transesterification, at identical contents.

In accordance with another variant of the process according to the present invention, the solvent (SL) is added at the end of the reaction, advantageously while the reaction product is at a temperature of from 60 to 90° C.

The process according to the invention, carried out in the transesterification or esterification reaction, thus advantageously leads to a liquid mixture which is homogeneous when hot in the said reactor, it then being possible for the said mixture to be emptied out easily by gravity into heated containers or into drums. By thus lowering the melting point of the acrylate (I) by mixing it with the solvent (SL), overheating of the pipes for transferring the mixture to the containers or drums and the risks of polymerization at the wall are avoided. Compared with the prior art:

the containers can be maintained at a lower temperature, which reduces the risks of polymerization during storage;

if the ester (I)/solvent (SL) mixture has been packaged in drums, the reheating of these drums in order to melt the product for a subsequent use is facilitated and the risks of polymerization are minimized.

The present invention advantageously leads to an ester (I)/solvent (SL) mixture which has a melting point that is at least 20° C. lower than that of the acrylate (I).

The examples which follow illustrate the present invention without, however, limiting its scope.

EXAMPLE 1

The following are loaded into a mechanically stirred reactor, heated using an electrical reactor heater, and over which is mounted a distillation column:

300 g of a heavy alcohol: linear $C_{18}$–$C_{40}$ alcohol, whose distribution is centred on the fraction $C_{28}$–$C_{32}$, with an alcohol content of 85% (the remaining 15% being saturated linear hydrocarbons), with an average molar mass, measured by OH number, of 460;

138.5 g of ethyl acrylate (ethyl acrylate/above alcohol molar ratio=2.5);

327 g of 1,2,4-trimethylbenzene (Solvesso 150);

0.17 g of hydroquinone monomethyl ether.

The reaction medium is dried by distilling off the water in the form of an ethyl acrylate/water azeotrope, after which 0.82 g of zirconium acetylacetonate is added.

The reaction is carried out under reduced pressure ($3.99 \times 10^4$–$2.66 \times 10^4$ Pa (300–200 mmHg)), at a temperature of between 100 and 120° C. The light alcohol (ethanol) is distilled off in the form of an ethyl acrylate/ethanol azeotrope, in order to shift the transesterification equilibrium in the direction of formation of the heavy acrylate.

When the reaction is complete, the excess ethyl acrylate is distilled off and an additional 169 g of 1,2,4-trimethylbenzene are added in order to have in the final mixture the desired mass percentage of 60%.

The final crude product, which is liquid and homogeneous when hot, in the reactor (808 g) is emptied out at about 70° C.

After cooling to room temperature, the final product is in the form of a solid which melts at about 48–50° C. (as opposed to 82–83° C. for the heavy acrylate).

This product can be stored at 48° C. or at room temperature (with, in this case, the need to remelt it before use), without any risk of polymerization.

EXAMPLE 2

Example 1 is repeated, loading all of the 1,2,4-trimethylbenzene at the end of the operation (after distillation followed by stripping off the ethyl acrylate).

The reaction is carried out as described in Example 1, under reduced pressure ($3.99 \times 10^4$–$1.33 \times 10^4$ Pa (300–100 mmHg)), at a temperature of between 100 and 120° C.

The residual ethyl acrylate is removed by distillation under $1.33 \times 10^4$ to $6.6 \times 10^3$ Pa (100 to 50 mmHg).

Additional stripping is then carried out under a pressure of $2.6 \times 10^3$ Pa (20 mmHg) while bubbling with air in order to strip off the residual traces of ethyl acrylate (<200 ppm in the final product).

496 g of 1,2,4-trimethylbenzene are then introduced into the reactor with stirring at 70–80° C., over 20 minutes.

The final mixture is emptied out at about 70° C.

809 g of a heavy acrylate/1,2,4-trimethylbenzene mixture having the same characteristics as in Example 1 are thus obtained.

EXAMPLE 3

Example 2 is repeated, replacing the 1,2,4-trimethylbenzene with xylene in heavy acrylate/xylene mass proportions=50/50.

The melting point of the final mixture is 59–60° C. (as opposed to 82–83° C. for the heavy acrylate).

EXAMPLE 4

The following are introduced into the apparatus described in Example 1, modified by adding a decanter at the top of the column:

300 g of the heavy alcohol used in Example 1;
41.9 g of acrylic acid;
150 g of toluene;
3.5 g of sulphuric acid taken as 100%;
0.17 g of hydroquinone monomethyl ether/0.17 g of hydroquinone.

Throughout the operation, gentle bubbling with air is maintained in the reactor.

The reaction is carried out under reduced pressure, at a temperature of between 90 and 115° C.

The water of reaction is distilled off in the form of a toluene/water azeotrope, in order to shift the esterification equilibrium in the direction of formation of the heavy acrylate. The toluene decanted off is permanently recycled into the reactor.

At the end of the reaction, the toluene is distilled off and the excess acrylic acid and the catalyst are neutralized with $Ca(OH)_2$.

493 g of 1,2,4-trimethylbenzene (60% by mass relative to the final product) are introduced into the reactor at about 85° C. over 20 minutes.

The crude product is emptied out while hot in the form of a liquid, through a heating filter.

The final mixture is in the form of a solid with a melting point of about 50° C.

What is claimed is:

1. A process for preparing and packaging at least one long-chain alkyl acrylate of formula (I):

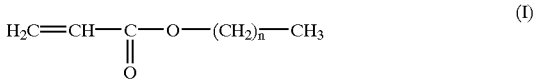
(I)

in which n is between 18 and 60,
comprising preparing the at least one long-chain alkyl acrylate of formula (I) in a reactor by transesterification between a light ester, which is liquid at room temperature, of formula (II):

(II)

in which $R^1$ represents $C_1$–$C_4$ alkyl and a heavy alcohol, which is solid at room temperature, of formula (III):

(III)

in which n is from 18 to 60,
in the presence of at least one transesterification catalyst and at least one polymerization inhibitor, while bubbling with air or depleted air, the light alcohol $R^1OH$ formed distilling off in the form of an azeotrope of light ester (II)/$R^1OH$, and the excess light ester (II) being removed by distillation at the end of the reaction, wherein the solvent (SL) is added to the initial load and/or after removal of the light ester (II), said solvent (SL) having a boiling point greater than that of the light ester (II) when it is introduced in total or in part with the initial load, forming a liquid homogeneous mixture of said at least one acrylate (I) and said solvent (SL), wherein the solvent is present in said mixture in a sufficient amount to provide said mixture with a melting point less than that of said acrylate (I), and packaging by emptying out said mixture from the reactor by gravity into a storage drum.

2. A packaging process according to claim 1, wherein solvent (SL) is inert with respect to the reaction medium into which it is introduced.

3. A process according to claim 1, wherein the solvent (SL) is chosen from aliphatic and aromatic hydrocarbons.

4. A process according to claim 3, wherein the solvent (SL) is chosen from xylenes, ethylbenzenes and trimethylbenzenes.

5. A process according to claim 1, wherein the solvent (SL) is introduced in an amount of 10 to 70% by weight, relative to the acrylate (I).

6. A process according to claim 1, wherein the solvent (SL) is added at the end of the reaction while the reaction product is at a temperature of from 60 to 90° C.

7. A process according to claim 1, wherein the ester (I)/solvent (SL) mixture has a melting point that is at least 20° C. lower than that of the acrylate.

8. A process according to claim 3, wherein the solvent is a petroleum fraction.

9. A process according to claim 5, wherein the solvent amount is 40 to 70% by weight of the acrylate.

10. A process according to claim 3, wherein the ester (I)/solvent (SL) mixture has a melting point that is at least 20° C. lower than that of the acrylate (I).

11. A process according to claim 4, wherein the ester (I)/solvent (SL) mixture has a melting point that is at least 20° C. lower than that of the acrylate (I).

12. A process according to claim 10, wherein the solvent (SL) is introduced in an amount of 10 to 70% by weight, relative to the acrylate (I).

13. A process according to claim 11, wherein the solvent (SL) is introduced in an amount of 10 to 70% by weight, relative to the acrylate (I).

14. A process according to claim 10, wherein the solvent amount is 40 to 70% by weight of the acrylate.

15. A process according to claim 11, wherein the solvent amount is 40 to 70% by weight of the acrylate.

16. A process according to claim 7, wherein the mixture is solid at room temperature.

17. A process for preparing at least one long-chain alkyl acrylate of formula (I):

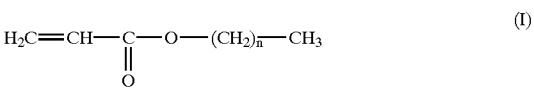
(I)

in which n is between 18 and 60,
and a mixture of said at least one long-chain alkyl acrylate of formula (I) and a solvent (SL)
comprising preparing the at least one long-chain alkyl acrylate of formula (I) by transesterification between a light ester, which is liquid at room temperature, of formula (II):

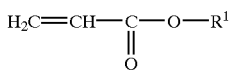
(II)

in which $R^1$ represents $C_1$–$C_4$ alkyl and a heavy alcohol, which is solid at room temperature, of formula (III):

 (III)

in which n is from 18 to 60, in the presence of at least one transesterification catalyst and at least one polymerization inhibitor, while bubbling with air or depleted air, the light alcohol $R^1OH$ formed distilling off in the form of an azeotrope of light ester (II)/$R^1OH$, and the excess light ester (II) being removed by distillation at the end of the reaction, wherein the solvent (SL) is added to the initial load and/or after removal of the light ester (II) to form a mixture, said solvent (SL) having a boiling point greater than that of the light ester (II) when it is introduced in total or in part with the initial load.

18. A process according to claim 17, wherein the solvent is introduced in the mixture in a sufficient amount to provide said mixture with a melting point less than that of said acrylate (I), wherein said solvent is inert with respect to the reaction medium into which it is introduced.

19. A process according to claim 17, wherein the solvent is chosen from aliphatic and aromatic hydrocarbons.

20. A process according to claim 17, wherein the solvent is chosen from the group consisting of xylenes, ethylbenzenes, and trimethylbenzenes.

21. A process according to claim 17, wherein the solvent is introduced in an amount of 10 to 70% by weight, relative to the acrylate (I).

22. A process according to claim 17, wherein the solvent (SL) is added at the end of the reaction while the reaction product is at a temperature of from 60 to 90° C.

23. A process according to claim 22, wherein it leads to a liquid mixture which is homogeneous when hot in the reactor, the said mixture then being emptied out by gravity into heated containers or into drums.

24. A process according to claim 17, wherein the ester (I)/solvent (SL) mixture has a melting point that is at least 20° C. lower than that of the acrylate (I).

25. A process according to claim 19, wherein the solvent is a petroleum fraction.

26. A process according to claim 21, wherein the solvent amount is 40 to 70% by weight of the acrylate.

27. A process according to claim 19, wherein the ester (I)/solvent (SL) mixture has a melting point that is at least 20° C. lower than that of the acrylate (I).

28. A process according to claim 20, wherein the ester (I)/solvent (SL) mixture has a melting point that is at least 20° C. lower than that of the acrylate (I).

29. A process according to claim 27, wherein the solvent (SL) is introduced in an amount of 10 to 70% by weight, relative to the acrylate (I).

30. A process according to claim 28, wherein the solvent (SL) is introduced in an amount of 10 to 70% by weight, relative to the acrylate (I).

31. A process according to claim 27, wherein the solvent amount is 40 to 70% by weight of the acrylate.

32. A process according to claim 28, wherein the solvent amount is 40 to 70% by weight of the acrylate.

33. A process according to claim 24, wherein the mixture is solid at room temperature.

34. A process according to claim 1, wherein the mixture is solid at room temperature.

35. A process according to claim 17, further comprising transferring the resultant mixture of said solvent and said at least one alkyl acrylate to a storage drum.

* * * * *